(12) United States Patent
Frisk et al.

(10) Patent No.: US 8,834,798 B2
(45) Date of Patent: Sep. 16, 2014

(54) ANALYSIS DEVICE

(75) Inventors: Thomas Frisk, Ingarö (SE); Wouter Van Der Wijngaart, Sollentuna (SE); Göran Stemme, Stockholm (SE); Per Månsson, Sundbyberg (SE)

(73) Assignee: Aerocrine AB, Solna (SE)

( * ) Notice: Subject to any disclaimer, the term of this patent is extended or adjusted under 35 U.S.C. 154(b) by 847 days.

(21) Appl. No.: 12/523,724

(22) PCT Filed: Jan. 18, 2008

(86) PCT No.: PCT/SE2008/050056
§ 371 (c)(1),
(2), (4) Date: Jan. 28, 2010

(87) PCT Pub. No.: WO2008/088289
PCT Pub. Date: Jul. 24, 2008

(65) Prior Publication Data
US 2010/0144059 A1    Jun. 10, 2010

(30) Foreign Application Priority Data
Jan. 19, 2007    (SE) ...................................... 0700182

(51) Int. Cl.
| G01N 33/497 | (2006.01) |
| G01N 33/00 | (2006.01) |
| G01N 21/35 | (2014.01) |
| G01N 33/543 | (2006.01) |
| G01N 29/02 | (2006.01) |
| G01N 27/407 | (2006.01) |
| G01N 29/22 | (2006.01) |
| G01N 21/78 | (2006.01) |
| G01N 21/65 | (2006.01) |
| G01N 21/55 | (2014.01) |
| A61B 5/08 | (2006.01) |
| G01N 1/22 | (2006.01) |
| G01N 21/77 | (2006.01) |
| A61B 5/097 | (2006.01) |

(52) U.S. Cl.
CPC .......... *G01N 33/54366* (2013.01); *G01N 21/78* (2013.01); *G01N 2291/0255* (2013.01); *B01L 2300/048* (2013.01); *G01N 21/65* (2013.01); *G01N 33/497* (2013.01); *G01N 33/0004* (2013.01); *G01N 21/3504* (2013.01); *G01N 21/553* (2013.01); *G01N 2291/0426* (2013.01); *G01N 21/783* (2013.01); *A61B 5/082* (2013.01); *G01N 33/4972* (2013.01); *G01N 1/2247* (2013.01); *G01N 2291/0256* (2013.01); *G01N 33/0009* (2013.01); *G01N 29/022* (2013.01); *G01N 33/0057* (2013.01); *G01N 2021/7786* (2013.01); *A61B 5/097* (2013.01); *G01N 27/4074* (2013.01); *G01N 29/222* (2013.01); *G01N 2291/0423* (2013.01)
USPC .......................................................... 422/83

(58) Field of Classification Search
CPC . G01N 33/497; G01N 33/007; G01N 21/783; G01N 15/1459; G01N 21/3504; G01N 33/0006; G01N 33/4972; G01N 2030/067; G01N 2033/4977; G01N 27/4074; G01N 31/224; G01N 33/0004–33/0073; G01N 33/98
USPC ......... 73/863.23, 597, 600, 23.2, 23.3, 19.03, 73/24.01, 24.04; 95/45; 96/4; 210/634; 435/287.2, 283.1, 287.1, 287.3, 287.9, 435/288.3–288.5; 436/178, 501, 514, 518, 436/523–536, 167, 168, 181
See application file for complete search history.

(56) References Cited

U.S. PATENT DOCUMENTS

| 3,788,486 | A * | 1/1974 | Bergstrom ................... 210/496 |
| 5,434,084 | A | 7/1995 | Burgess, Jr. |
| 8,017,408 | B2 * | 9/2011 | Meinhart et al. ............. 436/168 |
| 2003/0003587 | A1 | 1/2003 | Murray |
| 2005/0054078 | A1 | 3/2005 | Miller et al. |
| 2005/0233198 | A1 * | 10/2005 | Nuzzo et al. .................... 429/34 |
| 2006/0088857 | A1 * | 4/2006 | Attiya et al. ..................... 435/6 |
| 2006/0217893 | A1 | 9/2006 | Li et al. |

| | | | | |
|---|---|---|---|---|
| 2006/0249382 | A1* | 11/2006 | Hengstenberg et al. | 204/412 |
| 2007/0269893 | A1* | 11/2007 | Blankenstein et al. | 436/2 |
| 2010/0075347 | A1* | 3/2010 | Dasaratha et al. | 435/7.33 |

FOREIGN PATENT DOCUMENTS

| | | |
|---|---|---|
| JP | 11-142314 | 5/1999 |
| WO | WO 2006002469 A1 * | 1/2006 |
| WO | 2006/103439 A2 | 10/2006 |

OTHER PUBLICATIONS

Timmer et al., Selective Low Concentration Ammonia Sensing in a Microfluidic Lab-on-a-Chip, 2006, IEEE Sensors Journal, vol. 6, No. 3, pp. 829-835.*

Campbell, G. A. et al. (2006). "PEMC Sensor's Mass Change Sensitivity is 20 pg/Hz Under Liquid Immersion," *Biosensors and Bioelectronics* 22:35-41.

Desai, A. et al. (2000). "An Air-to-Liquid MEMS Particle Sampler," *IEEE*, pp. 733-738.

Frisk, T. et al. (2006). "A Micromachined Interface for Airborne Sample-to-Liquid Transfer and its Application in a Biosensor System," *Lab Chip* 6:1504-1509.

Gast, F.-U. et al. (2003). "The Development of Integrated Microfluidic Systems at GeSiM," *Lab Chip* 3:6N-10N.

International Search Report mailed May 14, 2008, for PCT Application No. PCT/SE2008/050056 filed Jan. 18, 2008, 4 pages.

Kosslinger, C. et al. (1992). "A Quartz Crystal Biosensor for Measurement in Liquids," *Biosensors & Bioelectronics* 7:397-404.

Michalzik, M. et al. (2005). "Miniaturized QCM-Based Flow System for Immunosensor Application in Liquid," *Sensors and Actuators B* 111-112:410-415.

Zhao, Y. et al. (2006). "Microparticle Sampling by Electrowetting-Actuated Droplet Sweeping," *Lab Chip* 6:137-144.

Extended European Search Report and Search Opinion received for European Patent Application No. 08705328.6, mailed on Feb. 24, 2012, 11 pages.

* cited by examiner

*Primary Examiner* — Melanie Y Brown
*Assistant Examiner* — Erik B Crawford
(74) *Attorney, Agent, or Firm* — Renner, Otto, Boisselle & Sklar, LLP

(57) ABSTRACT

There is provided an analysis device comprising a gas phase and a liquid phase and at least one sensor, said sensor having at least one point where an analyte is detected, said at least point being in contact with the liquid phase, characterized in that the device comprises a membrane with a first and a second side, which membrane is in contact with the gas phase on at least a part of one side of the membrane and which membrane is in contact with the liquid phase on at least a part of the other side of the membrane, wherein the membrane comprises openings, and wherein the largest possible distance between any two openings in the membrane is larger than the distance between the membrane and the point where an analyte is detected, moreover there is provided a method for analyzing an analyte in a gas phase.

27 Claims, 1 Drawing Sheet

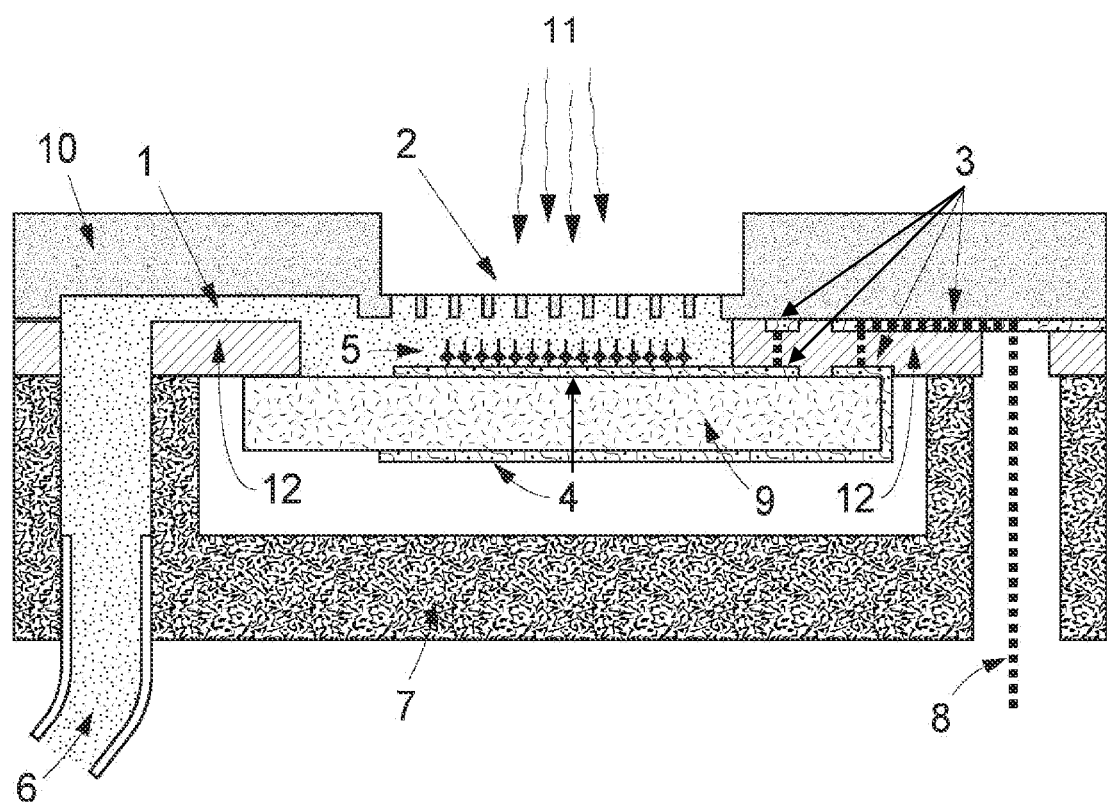

ANALYSIS DEVICE

CROSS REFERENCE TO RELATED APPLICATIONS

This is a U.S. National Phase patent application of PCT/SE2008/050056, filed Jan. 18, 2008, which claims priority to Swedish patent application Serial No. 0700182-9, filed Jan. 19, 2007, all of which are hereby incorporated by reference in the present disclosure in their entireties.

BACKGROUND

Detection and monitoring of airborne substances and analytes in a gas phase have become an important part in public health care, military and customs activities, security surveillance in public buildings and transportation, and in environmental monitoring. Physicians, the police, customs personnel, security personnel and others need detection equipment in order to detect the presence of various substances.

Previous analysis devices for analysing analytes in gas phase use three different absorption schemes. Firstly, the use of an open liquid reservoir with passive particle absorption has been suggested (M. Michalzik, R. Wilke and S. Büttgenbach, Sensors and Actuators B, 2005, 410-415), and (C. Kösslinger, S. Drost, F. Aberl, H. Wolf, S. Koch and P. Woias, Biosensors and Bioelectronics, 1992, 7, 397-404). Secondly, passively controlled surface tension based microfluidic interfaces for airborne sample-to-liquid absorption have been demonstrated (T. Frisk, W. v. d. Wijngaart, D. Rönnholm and G. Stemme, Lab On a Chip, 2006, 6, 1504-1509). Finally, systems with active liquid manipulation can be utilized to capture and transfer airborne particles to microfluidic systems. Desai et al. (A. Desai, S.-W. Lee and Y.-C. Tai, MEMS, 2000, 733-738) demonstrated airborne particle sampling with a liquid meniscus interface with DEP driven particle capture through the air-liquid interface. Recently, Zhao et al. (Y. Zhao and S. K. Cho, Lab On a Chip, 2005, 6, 137-144.) showed particle trapping with EWOD droplet sweeping.

Gast and Fiehn in Lab On a Chip, 2003, 3, 6-10, disclosed a chemical sensor comprising a sieve plate built into a channel system containing a microfluidic system.

The prior art regarding analysis devices for the analysis of analytes in a gas phase include several drawbacks. With open liquid reservoirs, the interfacial area is large but the sensitivity to external influence is large, since the gas liquid interface is easily disturbed. Such systems cannot offer robustness in terms of pressure variation tolerance or invariance to gravitation changes i.e. abrupt movement of the device. Surface tension based passive systems in the prior art can only offer a reduced possibility for a rapid response signal. There may also be problems with achieving an exposed area, which is sufficiently large.

Active liquid manipulation, utilize a moving liquid front, requiring manipulation of particles, the liquid and/or its constituents, with absorption taking place when the liquid reaches particles on the surface. The active liquid manipulation increases the complexity of such devices and negatively affects the potential for portability. Moreover the manufacturing costs increase.

Problems encountered in commercial sensors are long transport paths through tubing, valves, etc, resulting in reagent depletion through parasitic binding and in sample dispersion. Furthermore, difficulties in integration of many stand-alone components hinder development of portable instruments.

One problem in the state of the art regarding analysis devices comprising a quartz crystal microbalance is the sensitivity to external influence and stability.

SUMMARY OF THE INVENTION

It is an object of the present invention to address the disadvantages associated with known analysis devices and methods, and to provide an improved analysis device and a method for analysis of analytes in a gas phase, alleviating at least some of the problems in the prior art. Further disadvantages associated with known analysis devices and methods and the advantages associated with the embodiments of the invention will be apparent to a skilled person upon a closer study of the description, FIGURE, example and claims.

The present invention makes available an analysis device and a method as defined in the claims, incorporated herein by reference.

Further aspects of the invention, as well as their advantages, will become evident to the skilled person upon closer study of the description, example, claims and drawing.

SHORT DESCRIPTION OF THE DRAWING

The invention will be described in detail in the following description, non-limiting example, and claims, with reference to the attached drawing, FIG. 1, which shows a schematic cross sectional view of one embodiment of the invention.

DEFINITIONS

Before the present device and method is described in detail, it is to be understood that this invention is not limited to the particular configurations, method steps, detection methods, transducing methods, sensors and materials disclosed herein as such configurations, method steps, detection methods, transducing methods, sensors and materials may vary somewhat. It is also to be understood that the terminology employed herein is used for the purpose of describing particular embodiments only and is not intended to be limiting since the scope of the present invention will be limited only by the appended claims and equivalents thereof.

It must also be noted that, as used in this specification and the appended claims, the singular forms "a", "an", and "the" include plural referents unless the context clearly dictates otherwise. Thus, for example, a reference to a reaction mixture containing "an analyte" includes a mixture of two or more analytes.

The term "about" when used in the context of numeric values denotes an interval of accuracy, familiar and acceptable to a person skilled in the art. Said interval is preferably ±10%.

In describing and claiming the present invention, the following terminology will be used in accordance with the definitions set out herein.

The term "adhesive" as used throughout the description and the claims means a compound or composition that adheres or bonds two or more items together.

The term "adhesive tape" as used throughout the description and the claims means an adhesive coated onto a backing material such as paper, plastic film, cloth, or metal foil. Double-sided adhesive tape is able to adhere to objects on both sides of the tape.

The term "analyte" as used throughout the description and the claims means a substance, compound, chemical constituent or biological constituent that is determined in an analytical procedure. Examples of analytes include but are not limited to organic molecules, inorganic molecules, and atoms.

The term "analysis device" as used throughout the description and the claims means a device used to examine samples to gain understanding of their composition.

The term "anisotropic electric conductor" as used throughout the description and the claims means a directionally dependent conductor permitting the flow of electric current along at least one axis, but not along at least one other axis. Thus an example of an anisotropic electric conductor is a conductor that conducts electric current along the z-axis but not along the y-axis and the x-axis of an orthogonal coordinate system.

The term "hydrophobic" as used throughout the description and the claims refers to the physical property of a molecule or substance that is repelled from a mass of water. A hydrophobic surface repels water. Water on hydrophobic surfaces will exhibit a contact angle above 90°.

The term "hydrophilic" as used throughout the description and the claims refers to a physical property of a molecule or substance that can transiently bond with water through hydrogen bonding. This is thermodynamically favourable, and makes hydrophilic molecules soluble not only in water, but also in other polar solvents. Water on hydrophilic surfaces will exhibit a contact angle below 90°.

The term "hydrophilise" as used throughout the description and the claims means the process of making a surface more hydrophilic.

The term "hydrophobise" as used throughout the description and the claims means the process of making a surface more hydrophobic.

The term "Marangoni flow" as used throughout the description and the claims refers to flow on or in a liquid layer due to differences in surface tension.

The term "membrane" as used throughout the description and the claims means a separating layer. As used herein the term membrane includes but is not limited to membranes of all stiffness. Thus a very stiff diaphragm is encompassed by the term membrane as well as a very flexible membrane. A diaphragm is an example of a membrane. A membrane comprising openings allows the membrane to be selectively permeable.

DESCRIPTION

In a first aspect the present invention provides an analysis device comprising a liquid phase and at least one sensor, said sensor having at least one point where an analyte is detected, said at least point being in contact with the liquid phase, wherein the device comprises a membrane with a first and a second side, which membrane is in contact with a gas phase on at least a part of the first side of the membrane and which membrane is in contact with the liquid phase on at least a part of the second side of the membrane, wherein the membrane comprises openings, and wherein the largest possible distance between any two openings in the membrane is larger than the distance between the membrane and the point where an analyte is detected.

The sensor detects an analyte in at least one point. Such a point can be at the surface of the sensor or at a distance from the sensor. The point where the analyte is detected is in one embodiment the sensor surface, for instance when a quartz crystal microbalance is used. If for instance a sensor based on light is used, a point where the analyte is detected can be a distance apart from the sensor itself.

In one embodiment the sensor is in contact with the liquid, and in alternative embodiment the sensor is not in contact with the liquid, but the point where the analyte is detected is always in contact with the liquid.

The analysis device can advantageously be used for analysing analytes in a gas phase. An analyte in the gas phase reaches the gas liquid interface in the openings of the membrane. When the analyte is absorbed in the liquid phase the analyte diffuses towards the point where it is detected by the sensor. The addition of analyte and the addition of liquid to the analysis device are separated from each other. This makes it possible to manufacture an analysis device with a very short distance between the gas liquid interface and the point where the analyte is detected. One advantage of this is shorter diffusion times for an analyte from the gas phase to the point where it is detected by the sensor. One further advantage is that the loss of analyte is reduced. Another advantage is that no active means for transportation of the analyte are needed. The present device does not require any active means for the transport of analyte from the membrane to the point where the analyte is detected by the sensor. The transport of analyte from the membrane to the point where it is detected by the sensor takes place mainly by diffusion, heat convective transport and Marangoni flow. The transport is facilitated by a concentration gradient of the analyte.

In a preferred embodiment the distance from the membrane to the point where it is detected by the sensor is kept sufficiently short to avoid long transport times; therefore the largest possible distance between any two openings in the membrane should be larger than the distance between the membrane and the point where an analyte is detected. The largest possible distance between any two openings in the membrane is measured between openings which have maximal distance from each other. For a circular membrane the largest possible distance between any two openings is the distance from an opening on one side to an opening on the opposite side along the diameter of the circle. For a quadratic membrane the largest possible distance between any two openings is the distance from an opening in a corner to an opening in the opposite corner along the diagonal.

In one embodiment the largest possible distance between any two openings is a few millimeters. Examples of ranges which the largest possible distance between any two openings is within include but are not limited to about 0.01-10 mm, 0.1-5 mm, 1-5 mm, and 1-3 mm.

In one embodiment the membrane is pressed against a solid object or a substance in solid phase to be analysed. An analyte will then adsorb to the liquid interface and be transported through the liquid to the point where it is detected by the sensor.

In a further embodiment an analyte dissolved or suspended in a liquid is added on the membrane, on the side which is in contact with the gas phase.

In the present invention many different types of liquids can be used. In one embodiment the liquid is a mixture comprising more than one chemical compound. In one embodiment the liquid is polar and in an alternative embodiment the liquid is non-polar. In one embodiment the liquid is hydrophilic. In one embodiment the liquid is hydrophobic. In one embodiment the liquid is water. In another embodiment the liquid is oil. By oil is meant a hydrophobic, lipophilic or nonpolar liquid. In one embodiment the liquid is electrically conducting. In an alternative embodiment the liquid is not electrically conducting.

Examples of analytes which can be detected using the present invention include but are not limited to drugs, explosives, fungi, algae, pollen, cells, bacteria, virus, proteins, nucleic acids, DNA, RNA, and gases. Both analytes dissolved in the gas phase as well as particles and droplets present in the gas phase can be analysed.

The present invention allows analysis of an analyte in a gas phase as well as an analyte in liquid droplets in a gas phase. Moreover it allows analysis of an analyte in a liquid phase as well as an analyte in a solid phase.

In one embodiment the membrane comprising openings acts like a filter for large particles and objects.

In one embodiment the thickness of the membrane is in the range about 1-100 μm. In another embodiment the thickness of the membrane is in the range 10-50 μm. Other examples of ranges of suitable thicknesses include but are not limited to about 5-100 μm, 10-100 μm, 10-30 μm. In one embodiment the thickness is about 20 μm.

Surface energy provides robustness to the air-liquid interface, which is necessary for tolerating pressure and flow variations during operation that could lead to a collapse of the interface. Each opening functions as a static Laplace valve, keeping the liquid-gas interface in a fixed position. However, large negative or positive pressure loads can break the valve and subsequentially cause air introduction or flooding. In this context flooding means that liquid flows out of the system through at least one of the openings in the membrane. A smaller diameter of the openings allows for greater pressure loads before flooding or air introduction occurs. Controlled flooding of the device can be actively used in a rinsing procedure of the dry areas of the membrane, but should preferably not occur unintentionally.

In one embodiment the dimension of the openings in the membrane is selected so that the liquid does not flow out through the openings. The surface energy of the interface between the liquid and the gas prevents the liquid from flowing out through the openings. In one embodiment there is provided openings of elongated shape, such as slits or elongated ovals or elongated rectangles, where the distance from one side to another perpendicular to the elongated direction is less than about 200 μm, preferably less than about 150 μm, more preferably less than about 100 μm and most preferably in the interval about 10-40 μm. Openings of an elongated shape include but are not limited to slits.

In an alternative embodiment the greatest dimension of the openings is below about 200 μm. In one embodiment the greatest dimension of the openings is in the range about 1-40 μm. In another embodiment the greatest dimension of the openings is in the range about 1-30 μm. In another embodiment the greatest dimension of the openings is in the range about 10-40 μm. In a further embodiment the greatest dimension of the openings is in the range about 20-30 μm. The greatest dimension of the openings means the largest possible distance from one side of an opening to the other side of the same opening.

In one embodiment all openings are of about the same size. In an alternative embodiment the openings are of different sizes. In one embodiment all openings have about the same shape. In an alternative the openings have different shapes. The shape of the openings can be any shape. Examples of shapes include but are not limited to, circular, oval, triangular, square, pentagonal, hexagonal and polygonal.

In one embodiment the openings of the membrane are cylindrical. In this context there is defined a cross section in a plane perpendicular to the membrane surface. In one embodiment such a cross section is rectangular. In another embodiment the cross section of the openings is funnel-shaped or trapezoid. A cross section with larger area towards the gas phase has the advantage of a larger area of the gas liquid interface. Examples of techniques for the manufacture of openings include but are not limited to DRIE etching for cylindrical openings, etching with KOH for openings of trapezoidal cross section, and isotropic etching.

In one embodiment the openings are randomly distributed over the membrane. In one embodiment the openings are placed in a hexagonal pattern. One advantage of openings in a hexagonal pattern is that the mechanical strength and stiffness of the membrane is higher compared to other membranes with the same area of the openings.

In one embodiment the analysis device comprises at least one inlet for liquid. In one embodiment the analysis device also comprises at least one outlet for liquid.

Liquid may evaporate through the openings in the membrane. Liquid is in a one embodiment provided by a closed system so that a reservoir of liquid is in fluid contact with the space on one side of the membrane. The volume of the reservoir of liquid is preferably large compared to the volume of the space on one side of the membrane and compared to the evaporation. In a closed system at least one wall of the liquid reservoir can be made flexible to account for the decrease in the volume of liquid when the liquid leaves the reservoir. In an alternative embodiment liquid is provided from a liquid reservoir in fluid contact with the space on one side of the membrane in a system which is not closed. In an embodiment which is not closed there can be an opening in the liquid reservoir to let in gas when the liquid flows out of the reservoir. In one embodiment the liquid is added by passive means, which means that no external energy is added and that the addition is driven by another force or combination of forces such as evaporation of liquid, surface tension, or capillary force. Examples of a passive means include but are not limited to a reservoir of liquid located at a level above the space on one side of the membrane, and where the liquid can flow down to the space on one side of the membrane under the influence of gravity. Thus in one embodiment the analysis device comprises means for passive addition of liquid.

In another embodiment the analysis device comprises means for active addition of liquid. In another embodiment the analysis device comprises means for active removal of liquid. Also means for the simultaneous addition and removal of liquid are encompassed within the present invention. Examples of active addition and/or removal of liquid include but are not limited to addition of liquid with a pump or a piston. Examples include but are not limited to a membrane pump and a piston pump. In one embodiment liquid is added by heating a material which expands upon heating. The heat expandable material can be beads in the liquid reservoir and/or constitute at least a part of the walls of the liquid reservoir. When heated, a volume displacement is created which drives the flow of the liquid.

On the liquid side of the membrane there is at least one point where an analyte is detected by the sensor. The distance from the membrane to the point where an analyte is detected should be kept short so that an analyte in the gas phase can enter through at least one of the openings in the membrane and rapidly move through the liquid and reach the point where an analyte is detected by the sensor.

In one embodiment the membrane should not touch the sensor. When a quartz crystal microbalance is used as a sensor touching may disturb the sensor. In another embodiment the membrane can touch at least parts of the sensor, while still allowing a space for liquid between the membrane and the sensor. In one embodiment the distance between the membrane and the point where an analyte is detected is below about 1.0 mm. In another embodiment the distance between the membrane and the point where an analyte is detected is below about 500 μm. In yet another embodiment the distance between the membrane and the point where an analyte is detected is below about 200 µm. In one embodiment the distance is below about 100 µm. In a further embodiment the distance is below about 60 µm. In another embodiment said distance is about 10-100 µm.

In one embodiment the sensor and membrane are essentially parallel and opposite to each other. Thus the membrane and the sensor are facing each other, which facilitate the transport of an analyte from the openings in the membrane to the sensor. Essentially parallel means that the plane of the membrane and the plane of the sensor does not deviate more than 10°, preferably 5° from perfectly parallel planes. In one embodiment the sensor is a quarts crystal microbalance which is essentially parallel and opposite to the membrane.

The sensor is any sensor that can be used to detect an analyte in a liquid. In one embodiment the sensor is based on the principles of at least one selected from a quartz crystal microbalance, a surface plasmon resonance sensor, a Raman sensor, a surface acoustic wave sensor, a film bulk acoustic resonance sensor, a fluorescence based sensor, an electrochemical sensor, a colorimetric sensor, a luminescence based sensor and a photonic sensor. In one embodiment the sensor is based on the principles of one of the above mentioned sensors. In an alternative embodiment the sensor is based on the principles of several of the above mentioned sensors. In one embodiment the sensor is a quartz crystal microbalance. In one embodiment the sensor is an electrochemical cell. A synonym for QCM as used throughout this description and the claims is TSM which stands for thickness shear mode oscillator.

In one embodiment binding and/or release at the sensor of antigens and/or antibodies is detected. In one embodiment a mass change is detected.

In one embodiment an assay based on antibodies is used. Antigens are attached to the sensor, whereafter antibodies against the analyte to be detected are bound to the sensor. When the analyte to be detected diffuses towards the sensor a fraction of the antibodies will bind to the analyte and will be released from the sensor. A release of antibodies is detected. An addition of antigen is also detected.

In one embodiment antibodies and/or other reagents for modifying the surface of the sensor are added through the openings of the membrane. Addition through the openings of the membrane provides a faster addition compared to addition through an inlet for liquid.

In one embodiment the dead volume of the space between the membrane and the point where an analyte is detected is minimised. The dead volume is the volume of liquid which does not exchange or exchanges slower than other volumes when liquid is added through an inlet for liquid. One way of minimising the dead volume of the space between the membrane and the point where an analyte is detected is to select a suitable shape of the device so that added liquid easily can reach all parts of the space between the membrane and the point where an analyte is detected.

In some embodiments of the present invention different detection assays are used alone or in combination with at least one sensor. Examples of such assays include but are not limited to, an immunoassay based on antibodies, ELISA, chromatography, an electrochemical assay, and an immunohistological assay.

In one embodiment the analysis device further comprises a base and a protective cap, wherein the base, the protective cap and the sensor are connected to each other.

In one embodiment the analysis device further comprises a base and a protective cap, wherein the base, the protective cap and the sensor are connected by an adhesive.

In one embodiment the adhesive is an adhesive tape with adhesive on both sides. The use of a double sided adhesive tape has advantages when manufacturing the device, for instance because the manufacturing becomes easier.

In one embodiment the adhesive is an anisotropic electric conductor. The anisotropic electric conductor is used to achieve an electric connection between some electrodes on the parts which the adhesive is connecting, while at the same time providing insulation between other electrodes.

One embodiment of the present invention is depicted in FIG. 1. With reference to FIG. 1 this particular embodiment comprises a base 10 made of silicon, a membrane which is an integral part of the base and which membrane comprises openings 2. The device comprises a protective cap 7 and a quartz crystal microbalance 9. Further the device comprises an anisotropically conducting adhesive 12 connecting the quartz crystal microbalance 9 with the base 10 and also connecting the protective cap 7 with the base 10. The device further comprises gold contact pads 3 and electrodes 4 on the quartz crystal as well as an electric path 8 for conducting electric currents to and from the quartz crystal.

The pathway for electrical currents are indicated with dashed lines 8 in FIG. 1. In this embodiment the anisotropically conducting adhesive conducts current vertically so that electrodes placed opposite of each other are connected and other electrodes are insulated from each other. The adhesive is a liquid seal and holds the quarts crystal in correct position. The adhesive also holds the base and the protective cap together. The device further comprises channels for addition and removal of liquid. Only the addition channel 6 is shown in FIG. 1. The fluid channels comprise pillars (not shown) in the area 1 in order to prevent the adhesive to clog the fluid channel. The quartz crystal has attached antigens with antibodies bound to the antigens 5, which are a part of the assay. The sample comprising an analyte is in gas phase 11 and reaches the interface 2 and then moves to the assay molecules 5, where a mass change is detected by the quartz crystal microbalance 9. To the quartz crystal microbalance there are electrical connections to an appropriate analysis device to detect signals from the quartz crystal.

In one embodiment the device comprises fluid channels, which fluid channels comprise at least one selected from pillars, ridges, and protrusions.

In the embodiment depicted in FIG. 1 the base has four different functions, a) it is a frame on which the device is built up, b) it comprises the membrane, since the membrane is an integral part of the base, c) it comprises fluid channels, and d) it is equipped with electrical conductors and electrodes which create electrical contact with the sensor. Thus there is provided a device comprising a base, which base constitutes a frame on which the device is built up, wherein the membrane is an integral part of the base and wherein the base comprises fluid channels, and wherein the base comprises electrical conductors and electrodes. One advantage of this is that the device is easy to manufacture. Another advantage is that the device is easy to miniaturize. One further advantage is that the device can be manufactured in a cost efficient way.

In the embodiment depicted in FIG. 1 all parts are mechanically fixated by the anisotropically conducting adhesive 12. There is an opening in the adhesive to accommodate the space between the sensor and the membrane. One advantage of this is that the device is easy to manufacture.

In one embodiment the sensor is a quartz crystal microbalance and the quartz crystal is mechanically fixed only on one side of the crystal. In one such embodiment the crystal is mechanically fixed by an adhesive. The embodiment depicted in FIG. 1 is an example of a quartz crystal connected on one side only. The connection on one side only improves the properties of the quarts crystal microbalance. The sensitivity to external influences is thereby decreased. The stability is increased.

The membrane can be made of any suitable material or combination of materials. In one embodiment the membrane is made of at least one material selected from a semiconductor, a ceramic, a metal and a polymer. Examples of materials include but are not limited to silicon, and silicon carbide. Examples of metals include but are not limited to gold, stainless steel, platinum, aluminium, and brass (i.e. an alloy of copper and zinc). Examples of polymeric materials include but are not limited to polytetrafluoroethylene, polycarbonate, polymethyl methacrylate, and polyetheretherketone. Examples of ceramics include but are not limited to oxides, nitrides and carbides of different elements.

The stiffness of the membrane should be sufficient to withstand the forces acting on the membrane to a sufficient degree. At the same time the thickness should not be too large since the diffusion time of the analyte will increase and since the area on which the analyte may adsorb to will increase. The analyte may adsorb for instance to the sides of the openings. Therefore the stiffness and the thickness of the membrane should be optimised with regard to the material of the membrane and the intended use.

One parameter which has to be considered is the deflection of the membrane. This can occur during priming or sudden drying of the interface when exposed to a heat pulse. The amount of deflection under a certain pressure load is influenced by the membrane thickness, its radius, the size and pitch of the openings, and by the material properties given by the Young's modulus, and the Poisson's ratio. Young's modulus is a measure of the stiffness of a material. Poisson's ratio is the ratio of the relative contraction strain, or transverse strain (normal to the applied load), divided by the relative extension strain, or axial strain (in the direction of the applied load).

In one embodiment the membrane thickness and size of the membrane is chosen such that the maximum deflection is less than the spacing, between the membrane and the underlying crystal. Consideration must also be taken to the diameter and the shape of the openings since they strongly diminish the mechanical strength. Thus, from a pure mechanical viewpoint the membrane should be stiff, thick, and have a density of the openings to withstand deformations caused by pressure variations originating from the liquid flow and the capillary forces.

The membrane thickness and the size and shape of the openings also affect the total wet surface area around the point where an analyte is detected, which may act as a parasitic binding area for an analyte, thus reducing the available amount of reacting analyte in the analysis device. The size and shape of the openings also affect the total dry membrane surface area, which may collect airborne molecules.

After absorption of an analyte at the air-liquid interface, the molecules must move through the openings and the layer of liquid to reach the point where an analyte is detected. This is influenced by diffusion, heat convective transport and Marangoni flow or any other transport mechanism. The total transportation length, i.e. the distance from the air-liquid interface to the surface of the sensor, is critical since it greatly affects the transport time. The distance must be chosen to allow for a fast transport of an analyte to the sensor surface and thereby enable a rapid analysis of the sample.

The presence of analytes and other substances can cause a shift in surface tension of the liquid.

Dry-out of the liquid may cause deterioration of a coating on the sensor, depending on the type of sensor used, but with a continuous flow of liquid the problem is easily solved. Another feature of a continuous flow of liquid is to wash away unbound molecules at the sensor. The flow rate has an upper limit as there must be sufficient time for the sample to diffuse and interact with the sensor. The lower flow rate limit is set by the allowable time to reset the chemical conditions in the liquid, e.g. between two separate measurements, but also to sustain the chemical conditions during active measurements, e.g. to prevent changes in salinity due to evaporation upon heating.

In one embodiment the membrane comprises a thin membrane in combination with reinforcements of the same material or at least one further material. In one embodiment there is provided a polymeric membrane which is 0.01-10 µm, preferably 1-10 µm thick with openings, which is placed on another material with much larger openings.

In one embodiment the membrane comprises at least one membrane and at least one reinforcement.

The surface tension, or the surface free energy, is of importance for the functionality of the microfluidics of the device. From a fluidic perspective, one would ideally like to have the wetted areas of the device hydrophilic (contact angle <90°) to allow for easy and rapid filling when using aqueous solutions. However, the dry areas of the membrane should preferably be hydrophobic (contact angle >90°) to increase the pressure at which the liquid flows out through the openings, i.e. robustness against flooding. The surface character of the materials in the device also affects the amount of parasitic binding and consequently loss of analyte. Surface modifications and chemical treatments of the materials are possible, e.g. through passivation, oxidation, adding blocking agents, hydrophilising, hydrophobising etc., to reduce the parasitic effects.

When using a hydrophobic liquid the hydrophobic and hydrophilic areas should be adapted with regard to the properties of the liquid. Also the properties of the analyte should be taken into account when designing the properties of the surface. In one embodiment the adsorption of an analyte to the walls of the device are minimised by selecting a hydrophobic or hydrophilic surface depending on the properties of the analyte.

In one embodiment at least a part of the membrane is hydrophilised. In one embodiment at least a part of the membrane is hydrophobised. In one embodiment hydrophilisation of a part of the membrane is combined with hydrophobisation of another part of the membrane. In another embodiment at least a part of the membrane is hydrophobic and at least a part of the membrane is hydrophilic. In one embodiment intended for use with polar solvents the side of the membrane facing the polar liquid is hydrophilised and the side of the membrane facing the gas phase is hydrophobised. In an alternative embodiment intended for hydrophobic liquids the side of the membrane facing the liquid is hydrophobised and the side of the membrane facing the gas phase is hydrophilised.

In one embodiment the device comprises fluid channels, which fluid channels comprises pillars and/or ridges and/or protrusions. One advantage of this is that if an adhesive is used it can not easily enter the fluid channel.

In one embodiment the device is provided with further electrodes so that charged particles in the gas phase are driven towards the membrane. In one embodiment one electrode is placed on the membrane or in the liquid and the other corresponding electrode is placed in the gas phase at a distance from the membrane. In an alternative embodiment the membrane itself constitutes the electrode, and is thereby electrically conducting. This technology is electrohydrodynamic pumping (EHD). Examples of applied voltages include but are not limited to voltages in the range about 1000-100000 volts. Examples of distances between the electrodes include but are not limited to distances in the range about 1-50 cm.

In a second aspect of the present invention there is provided a method for analysing an analyte in a gas phase, said method comprising addition of a liquid to an analysis device according to the present invention, wherein a liquid stream is added through at least one inlet and wherein an analyte enters through openings of a membrane into the device, separate from the liquid stream.

One advantage of the separate addition of analyte and liquid is that a mixture of liquid and analyte does not have to be actively handled, which avoids a number of disadvantages including long handling times and parasitic adsorption.

In one embodiment the liquid stream flows forward and is reversed at least once. The flow can flow back and forth several times. One advantage of the forward and backward flow is that bubbles of gas in the liquid escape through the openings in the membrane.

Example 1

Narcotics Detection

The device used in example 1 consists of a quartz crystal mounted to a silicon chip as a base and covered by a protective polymer cap by using double-sided vertically conductive adhesive foil (VCAF), as schematically depicted in FIG. 1. The base serves several functions: it gives rigid support to all device components, it accommodates microchannels for transport of liquid and electrical paths to the crystal electrodes through the VCAF, and it defines a robust air-liquid interface where airborne molecules can become absorbed into the liquid. The quartz crystal is a shear mode electromechanical oscillator, with the resonance frequency dependent on the mass of the material attached to its surface. Piezoelectric excitation is provided through the top and base electrodes with wrap-around contact pads. The VCAF adhesively bonds both the quartz crystal and the protective polymer cap to the base. The anisotropically conductive property of the adhesive provides electrical connection between the base and the QCM, and electrical isolation to the rest of the system, which allows for easy external contacting to the device. The polymer cap gives protection to the QCM from external influences without making any mechanical contact to it. Through the cap, electric and fluidic connections are made and direct exposure of the sensing parts of the device is avoided.

The largest possible distance between any two openings of the membrane was 5 mm. The thickness of the membrane was 20 μm. The distance between the membrane and the sensor was 50 μm. The diameter of the openings was 23 μm. The openings were of equal shape and size and placed in a hexagonal pattern.

The sensor is based on a QCM with a competitive immunoassay developed by Biosensor Applications AB, Solna, Sweden. The assay consists of drug molecules, antibodies (Ab), and surface immobilized antigens (Ag). The antibodies have a higher affinity to the drug molecules than to the antigens and consequently more Ab-drug than Ab-Ag complexes are formed in the presence of all three types of molecules. This assay is used to enhance the signal read-out, i.e. change in mass at the sensor surface, upon detection of drug molecules since the antibodies have a larger mass than the drug molecules.

The device was coupled in a fluidic setup with a liquid reservoir upstream, and a syringe pump downstream. A phosphate buffer saline (PBS) solution, 137 mM NaCl, 10 mM Phosphate, 2.7 mM KCl, pH 7.4 was continuously hydrostatically pumped through the two fluidic ports of the device at 0.35 μl/min. 50 μl antibody solution (anti-MDMA (ecstasy) or anti-cocaine IgG, 0.1 g/l in PBS, Biosensor AB, Solna, Sweden) was applied onto the air-liquid sample interface, brief washing step with PBS followed. Fiberglass filter sheets (Biosensor AB, Solna, Sweden) containing drug traces were positioned approximately 500 μm above the interface. They were exposed to an 8 s heat pulse of 270° C. (cocaine) or 5 s at 350° C. (MDMA) to evaporate the sample from the filter. Upon interaction of the sample with the antibodies on the QCM, a custom made oscillator circuit measured the baseline frequency shift. Consecutive measurements with 200 ng and 300 ng ecstasy on the filter resulted in a respective baseline shift of 50 and 44 Hz, whereas blank filter runs resulted in a signal level of at least an order of magnitude lower (<5 Hz, within noise limits). A third run with 200 ng ecstasy sample yielded 10 Hz. The decrease in signal is most likely caused by a depletion of antibodies on the QCM surface. However, this run shows that the surface is not completely depleted of antibodies. Similar system tests were also successfully performed with cocaine-prepared filters targeted at QCMs prepared with cocaine-Ag and cocaine-Ab chemistry.

The frequency shift response in tests with cocaine (~5 Hz/100 ng) and with ecstasy (~15 Hz/100 ng) corresponds to a sensitivity of at least 20 ng/Hz and 6 ng/Hz, respectively. The sensitivity level is limited by noise, which was measured during blank runs to approximately 5 Hz, and by temperature and pressure fluctuations.

In this device, as in similar devices, capillary action and surface tension are dominating over gravity, thus the device is largely insensitive to moves, tilts, turning and repositioning. This results in a robust device that tolerates manual handling. The size and weight of the device and its low manufacturing cost can be compared to commercially available systems that are large, heavy and expensive. Thus, the presented device fulfils foreseen demands on a handheld device for drug detection.

The assay chamber contains 0.98 μl and the openings 0.21 μl. A 10 minutes run will use 3.5 μl of PBS and the chamber liquid volume will be refreshed 3 times. Thus, large liquid reservoirs are unnecessary which facilitates the use of the device in portable applications. In our experimental setup, we found the response time, i.e. the time between the start of the heat pulse and the time of a stable readout signal, to be approximately 25 s, where the heat pulse accounts for 5 or 8 s and the diffusion time for less than 5 s (estimated). In many security or health care applications a response time of 30 s is acceptable. As the detection chemistry relies on a liquid based immunoassay with drug molecules, antigens, and antibodies the inventors believe, without being bound by any specific scientific theory, that molecular diffusion is the dominant sample transport mechanism.

Example 2

Detection of a Component in Exhaled Breath

The analysis device according to the present invention can be used to analyse components in gas exhaled from a human or an animal. Examples of analytes include but are not limited to inflammation indicating substances, endogenous inflammation indicating substances and NO. One example of a sensor includes but is not limited to an electrochemical cell.

Although the invention has been described with regard to its preferred embodiments which comprise the best mode presently known to the inventors it should be understood that various changes and modifications as would be obvious to one having the ordinary skill in this art may be made without departing from the scope of the invention as set forth in the claims appended hereto.

The invention claimed is:

1. An analysis device comprising:
   a liquid phase;
   a sensor, said sensor having at least one point where an analyte is detected, said at least one point being in contact with the liquid phase;
   a membrane with a first side and a second side, which membrane is in contact with a gas phase containing the analyte on at least a part of the first side of the membrane and which membrane is in contact with the liquid phase on at least a part of the second side of the membrane, the second side juxtaposed with the sensor and spaced apart from the sensor by the liquid phase and wherein the membrane comprises openings, an interface between the liquid phase and the gas phase located at each opening, the analyte entering the liquid phase from the gas phase via the openings for detection by the sensor and wherein the largest possible distance between any two openings in the membrane is larger than the distance between the membrane and the point where the analyte is detected.

2. The analysis device according to claim 1, wherein the thickness of the membrane is in the range of 1-100 µm.

3. The analysis device according to claim 1, wherein the distance between the membrane and the point where the analyte is detected is below 1 mm.

4. The analysis device according to claim 1, wherein the sensor is in contact with the liquid.

5. The analysis device according to claim 1, wherein the sensor and membrane are essentially parallel and opposite to each other.

6. The analysis device according to claim 1, wherein the openings are placed in a hexagonal pattern.

7. The analysis device according to claim 1, wherein liquid is provided to the analysis device from a closed system.

8. The analysis device according to claim 1, wherein the analysis device comprises at least one inlet for liquid.

9. The analysis device according to claim 8, wherein the analysis device comprises at least one outlet for liquid.

10. The analysis device according to claim 8, wherein the analysis device comprises means for active addition of liquid.

11. The analysis device according to claim 9, wherein the analysis device comprises means for active removal of liquid.

12. The analysis device according to claim 1, wherein the sensor is selected from the group consisting of a quartz crystal microbalance, a surface plasmon resonance sensor, a Raman sensor, a surface acoustic wave sensor, a film bulk acoustic resonance sensor, a fluorescence based sensor, an electrochemical sensor, a colorimetric sensor, a luminescence based sensor and a photonic sensor.

13. The analysis device according to claim 12, wherein the sensor is the quartz crystal microbalance.

14. The analysis device according to claim 1, wherein the analysis device further comprises a base and a protective cap, wherein the base, the protective cap and the sensor are connected by an adhesive.

15. The analysis device according to claim 14, wherein the adhesive is an adhesive tape with adhesive on both sides.

16. The analysis device according to claim 14, wherein the adhesive is an anisotropic electric conductor.

17. The analysis device according to claim 13, wherein the sensor is the quartz crystal microbalance and wherein the quartz crystal is mechanically fixed only on one side of the crystal.

18. The analysis device according to claim 1, wherein the membrane is made of at least one material selected from the group consisting a semiconductor, a ceramic, a metal, a polymer, silicon, silicon carbide, gold, stainless steel, platinum, aluminium, brass, polytetrafluoroethylene, polycarbonate, polymethylmethacrylate, polyetheretherketone, a nitride and a carbide.

19. The analysis device according to claim 1, wherein the membrane comprises at least one membrane and at least one reinforcement.

20. The analysis device according to claim 1, wherein at least a part of the membrane has been hydrophilised.

21. The analysis device according to claim 1, wherein at least a part of the membrane has been hydrophobised.

22. The analysis device according to claim 1, wherein at least a part of the membrane is hydrophobic and wherein at least a part of the membrane is hydrophilic.

23. The analysis device according to claim 1, wherein said device comprises a fluid channel, which fluid channel comprises at least one selected from the group consisting of pillars, ridges, and protrusions.

24. The analysis device according to claim 1, further comprising a base, which base constitutes a frame on which the device is built up, wherein the membrane is an integral part of the base and wherein, wherein the base comprises fluid channels, and wherein the base comprises electrical conductors and electrodes.

25. The analysis device according to claim 1, further comprising at least one electrode on or near the membrane and at least one further electrode at a distance from the membrane.

26. The analysis device according to claim 1, wherein the greatest dimension of the openings in the membrane is below 200 µm.

27. The analysis device according to claim 1, further comprising an adhesive layer, and wherein the membrane is part of a member that is secured to the sensor with the adhesive layer, the adhesive layer spacing the membrane and sensor apart and forming sidewalls of a cavity for the liquid phase that is interposed between the second side of the membrane and the sensor.

* * * * *